(12) United States Patent
Lochte et al.

(10) Patent No.: US 6,758,839 B2
(45) Date of Patent: *Jul. 6, 2004

(54) TAMPON FOR FEMININE HYGIENE OR MEDICAL PURPOSES, AND PROCESS FOR PRODUCING THE SAME

(75) Inventors: Karin Lochte, Wuppertal (DE); Hans Werner Schoelling, Ennepetal (DE); Andrew L. Lewis, Farnham (GB)

(73) Assignee: Johnson & Johnson GmbH (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/204,696

(22) Filed: Dec. 3, 1998

(65) Prior Publication Data

US 2002/0026177 A1 Feb. 28, 2002

(30) Foreign Application Priority Data

Dec. 3, 1997 (DE) .......................................... 197 53 665

(51) Int. Cl.[7] .................................................. A61F 13/20
(52) U.S. Cl. .................... 604/385.18; 604/370; 604/904
(58) Field of Search ................................. 604/904, 370, 604/385.17, 385.18

(56) References Cited

U.S. PATENT DOCUMENTS

| 3,683,912 A | | 8/1972 | Olson et al. ............... 128/285 |
|---|---|---|---|
| 3,815,601 A | * | 6/1974 | Schaefer ..................... 604/904 |
| 3,902,493 A | * | 9/1975 | Baier et al. ................. 604/904 |
| 4,056,103 A | | 11/1977 | Kaczmarzyk et al. ....... 128/285 |
| 4,211,225 A | * | 7/1980 | Sibalis ........................ 604/904 |
| 4,305,391 A | | 12/1981 | Jackson ...................... 128/270 |
| 4,475,911 A | * | 10/1984 | Gellert ........................ 604/904 |
| 4,699,618 A | | 10/1987 | Sustmann ................... 604/365 |
| 4,816,100 A | * | 3/1989 | Friese ......................... 604/904 |
| 4,859,273 A | * | 8/1989 | Friese ......................... 604/904 |
| 4,863,450 A | * | 9/1989 | Friese ......................... 604/904 |
| 5,366,450 A | | 11/1994 | DeGroot ..................... 604/366 |
| 5,374,258 A | | 12/1994 | Lloyd et al. ................ 604/358 |
| 5,817,077 A | | 10/1998 | Foley et al. ................ 604/363 |

FOREIGN PATENT DOCUMENTS

| AU | 74346/91 | 10/1991 |
|---|---|---|
| DE | 35 19 515 A | 12/1986 |
| DE | 90 15 123 | 11/1990 |
| EP | 0 124 834 A2 | 11/1984 |
| EP | 0 149 155 A2 | 7/1985 |
| EP | 0 215 417 A1 | 3/1987 |
| EP | 0 553 966 A1 | 8/1993 |
| EP | 0 564 681 A1 | 10/1993 |
| EP | 0 685 213 A2 | 12/1995 |
| GB | 1 218 641 | 1/1971 |
| WO | WO 95/16423 | 6/1995 |

OTHER PUBLICATIONS

ASTM Standard, Edition D 1894–95 –Standard Test Method for Static and Kinetic Coefficients of Frictionof PlasticFilm and Sheeting, pp. 469–473.

* cited by examiner

*Primary Examiner*—Dennis Ruhl

(57) ABSTRACT

A tampon for feminine hygiene or medical purposes comprising a nonwoven cover having at least one, outwardly directed, smooth surface and substantially enclosing a liquid absorbing core wherein the nonwoven cover comprises at least partly thermoplastic, heat-sealable fibers and pressed to the final shape of the tampon. Before the tampon blank is covered with the nonwoven covering web, said web was subject to the use of heat and pressure during the manufacturing of the tampon as to smooth out at least the outer surface of the nonwoven covering web, whilst maintaining the structure of the nonwoven covering web and the absorbency of the tampon. Thereby, it is achieved that the tampon can also be more easily and more comfortably introduced into and withdrawn from a body cavity before and after the days of stronger menstruation or at the occurance of only less vaginal exudation as garment protection.

15 Claims, 8 Drawing Sheets

FIG. 1
(A) Original material
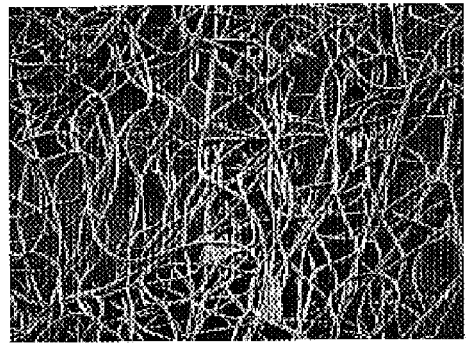
x 50
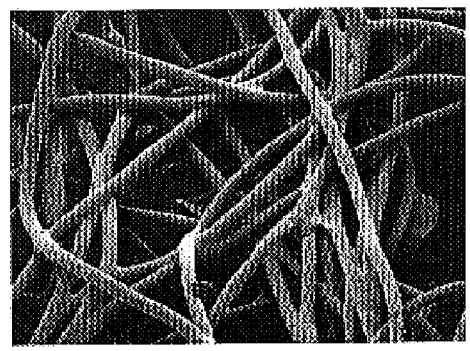
x 200
x 1000
(B) Calendered non-woven
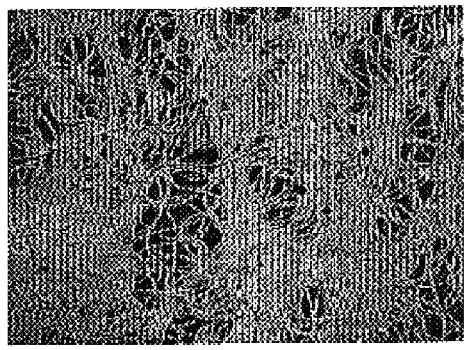
x 50
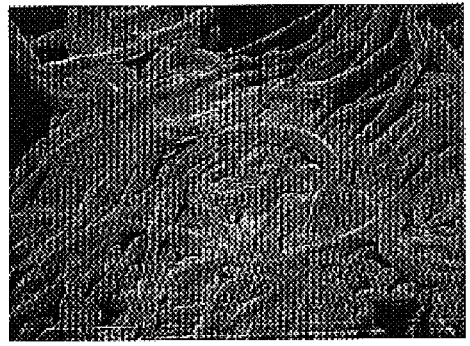
x 200
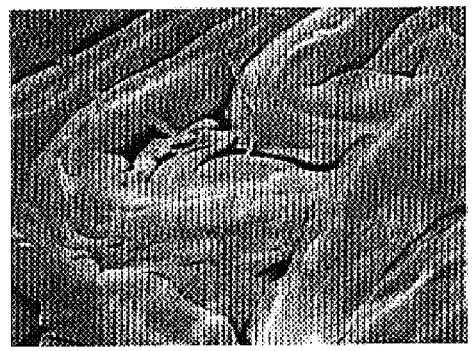
x 1000

Thickness of the calendered and uncalendered non-woven

Smoothness of calendered and uncalendered non-woven

Permeability of calendered and uncalendered non-woven

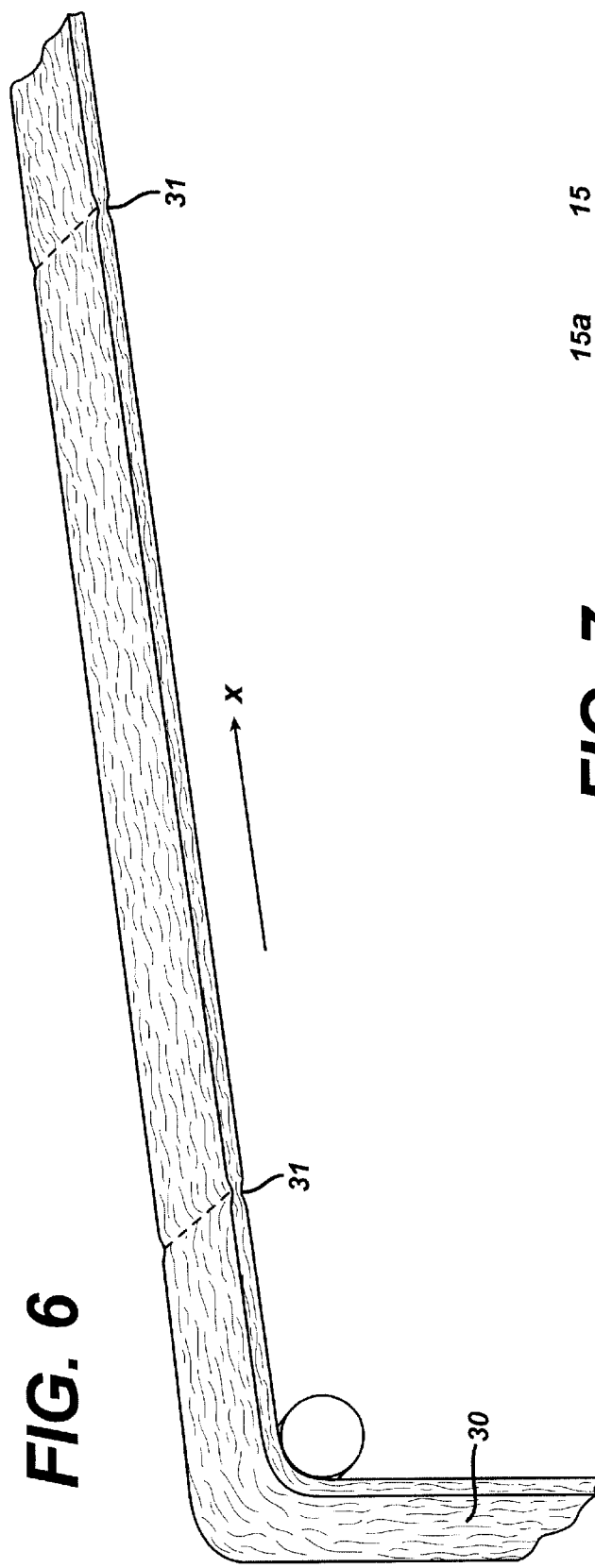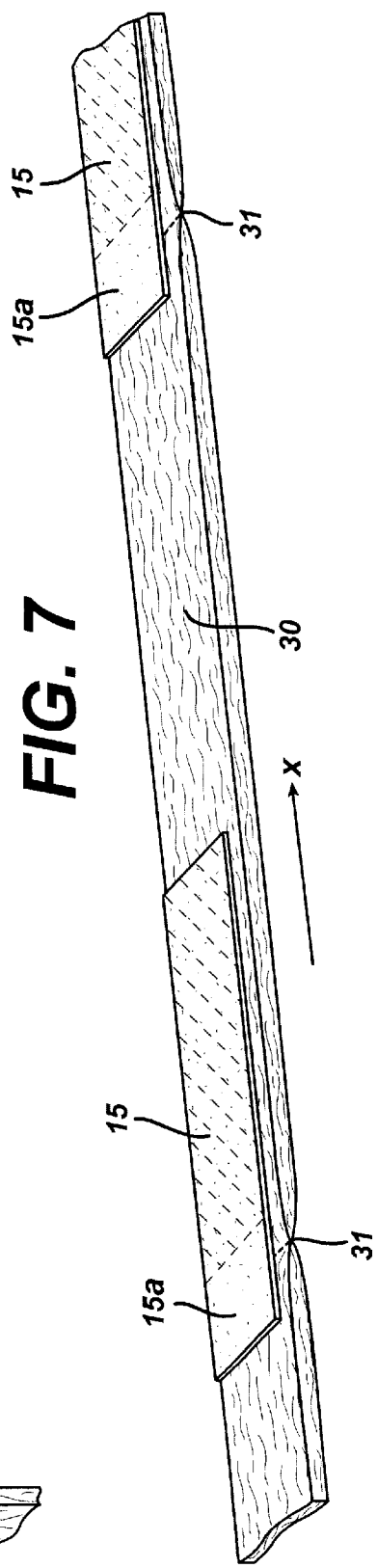

FIG. 13
FIG. 14
FIG. 15
FIG. 16
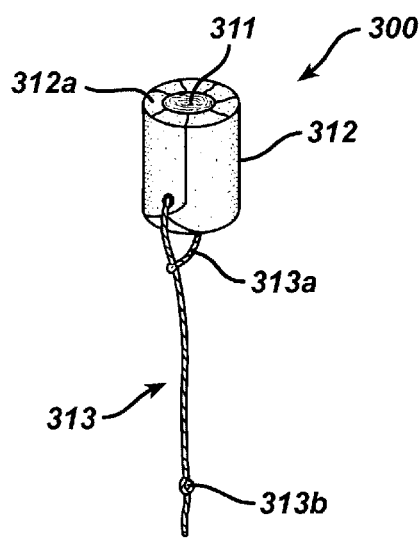
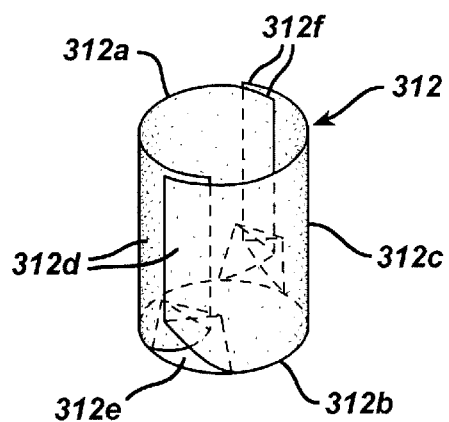
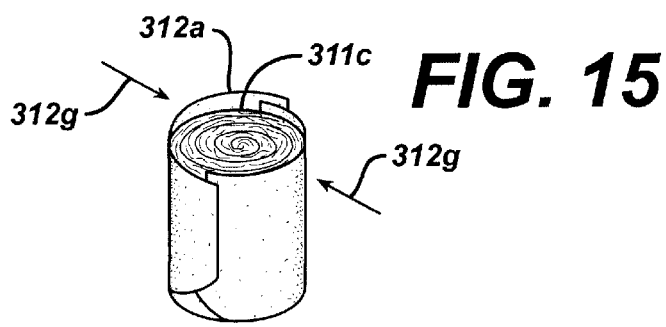
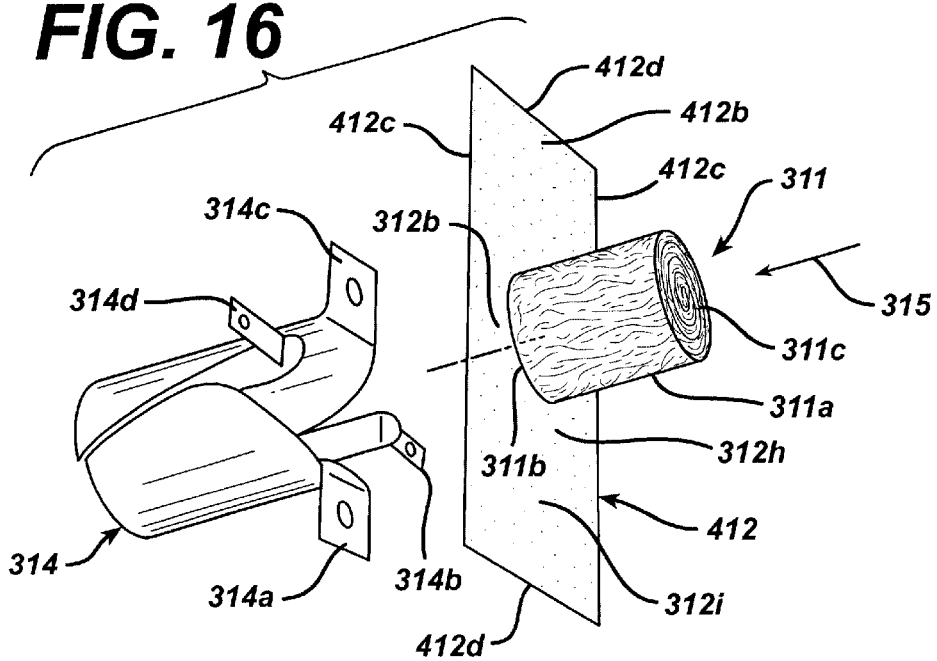

ABSORBENT STRUCTURE## TAMPON FOR FEMININE HYGIENE OR MEDICAL PURPOSES, AND PROCESS FOR PRODUCING THE SAME

FIELD OF INVENTION

The invention relates to a tampon for feminine hygiene or medical purposes, and to a process for producing the same. The tampon, which is suitable for mass production, comprises a compressible tampon blank of liquid-absorbing material and an at least partial covering for the latter made of a liquid-permeable nonwoven material made of, at least partly thermoplastic, heat-sealable fibers, and is pressed into the final shape of the tampon.

Tampons customarily contain hydrophilic materials in the form of fibers or foams and are compressed into a generally cylindrical shape. It is known that the insertion of such a structure into the vagina is often difficult and uncomfortable because of the roughness and dryness of the surface texture of the absorbent core. If the absorbent core is also composed of fibrous materials, the fibers have the tendency to become detached during the insertion and the removal of the tampon from the body. Problems associated with insertion can be overcome to a certain extent by the use of an applicator for tampons that are provided for this; however, the use of applicators does not solve the problems associated with the loss of fibers or when removing the tampon. EP-B 0 149 155 and GB-B 1 218 641 relate to the use of a liquid-permeable covering layer, which encloses the absorbent core and reduces the fiber loss. In addition, the covering layer can reduce the surface friction by covering the absorption core located underneath it, and can contribute to more agreeable insertion and removal of the tampon.

Normally, the outer or covering layer itself is constituted by a nonwoven material, which has an essentially open, liquid-permeable structure and which is easier to produce (EP 0 149 155). In recent times, in many cases the covering layer materials have been developed in particular with regard to the improvement of the insertion properties, for example the covering consisting of polypropylene (PP) which is described in U.S. Pat. No. 3,683,912, or the powder-bonded material in Australian Patent 74346/91. In addition, it has been established that similar advantages can be achieved using materials other than nonwovens, such as network-like structures, which are described in U.S. Pat. No. 5,374,258. In a similar way, there are examples of covering layer or enveloping materials which have been developed in order to make the removal of the tampon easier. The absorbent core of the tampon is responsible for bringing about a high capillary suction in the vagina, as a result of which the removal of the tampon is often made more difficult and is disagreeable. Covering layers serving for easier removal solve this problem by means of methods of reducing the suction action, such as a more effective covering of the absorbent core, such as for the double-enveloped tampon which is described in U.S. Pat. No. 4,305,391, or by holding back liquid in the fibers of the covering layer in order to maintain a soft and supple surface, as in U.S. Pat. No. 4,056,103.

SUMMARY OF THE INVENTION

The present invention relates to a tampon and to processes for its production. The tampon according to the invention comprises an absorbent body of nonwoven fibers and a liquid-permeable, thermoplastic covering material which at least partly covers the latter and which is pressed radially to the final shape of the tampon. The covering material is fitted to the absorption body, and the entire structure is wound up to form a so-called tampon blank. The blank is pressed radially and a sharp taper may be formed at the insertion end, in order to impart the final form to the tampon.

Thermoplastic, nonwoven materials often constitute the desired material for tampon coverings, since they can easily be fastened to the tampon during production by applying heat and/or pressure (U.S. Pat. No. 4,863,450, which is herein incorporated by reference). Nonwoven materials which are produced from bicomponent fibers are particularly suitable for this process, since the polymer having the lower melting point, which forms one component of the fiber (often about 50% of the overall fibers in the form of a covering layer), melts, in order to form a fastening to the substrate lying beneath it, while the component having a higher melting point (often the fiber core) maintains its physical characteristic, in order to maintain the integrity of the covering.

An object of the invetnion is to improve a tampon, which is at least partly surrounded by a nonwoven covering tape, in such a way that, even before and after the days of relatively heavy menstruation, or in the case of only slight vaginal discharges occurring, it can be inserted more easily and more agreeably, as lingerie protection, into a body cavity and can also be removed again from the latter.

It has been established that smoothing the wholly or partially thermoplastic, nonwoven covering web by calendering under the influence of heat and pressure, this smoothing being integrated into the continuous mass production of tampons, provides a singular opportunity, without penalties in terms of production speed, to adapt the smoothing of the nonwoven covering web, by means of extremely fine control, to the respective tampon to be produced, and to optimize the said smoothing from the point of view of availability, quality requirements and quality control, reduction of waste and availability, for example from the point of view of necessary corrections to the dimensions.

Nonwoven materials comprising bicomponent fibers, or even nonwoven materials which are composed of a combination of fiber types having considerably different melting points and cross-sectional shapes, and which have either previously been bonded by calendering by means of a process such as air-laying or thermal bonding, or are supplied as a non-bonded web directly from a carder, can be led through the gap in a calender unit during the continuous mass production of tampons, the said calender unit being composed of two smooth rolls which apply pressure and temperature below the melting point to the fiber component having the lower melting point. The resulting material is a very smooth and glossy product, which not only provides the easing described during insertion, wearing and removal of the tampon, but in addition also has a pleasing appearance.

BRIEF DESCRIPTION OF THE DRAWINGS

FIG. 1 shows electron-microscope images of the structure of a nonwoven covering web for a tampon according to the invention, at various enlargements;

FIGS. 6 to 11 show steps in a process for producing a first tampon according to the invention;

FIG. 13 shows a perspective view of a second embodiment of a tampon blank having a nonwoven covering web section surrounding the said blank;

FIG. 14 shows an enlarged view of the nonwoven covering web section before one edge is folded (turned in);

FIG. 15 shows an enlarged view of the tampon blank and of the nonwoven covering web section in FIG. 14 before a retrieval string is fitted;

FIG. 16 shows an exploded drawing of an apparatus for producing a second embodiment of a tampon according to the invention, having a nonwoven covering web section made of liquid-permeable material, on one side of which a tampon blank and on the other side of which a folding die plate are arranged.

DETAILED DESCRIPTION OF PREFERRED EMBODIMENTS

Figure 2:
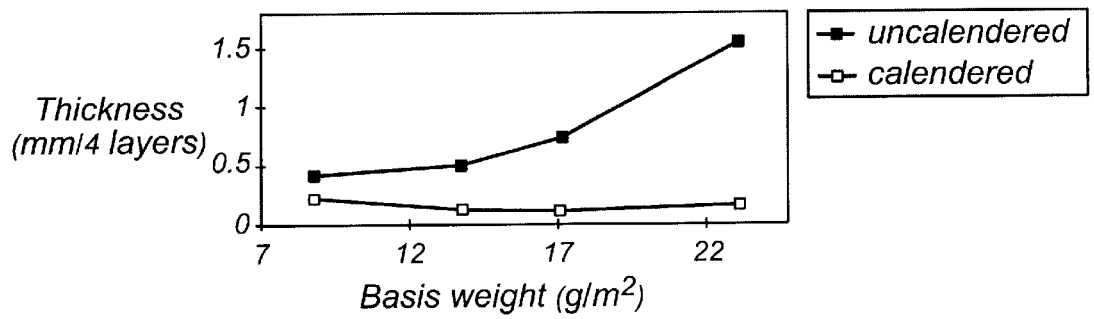
FIGS. 2 to 4 show diagrams which illustrate properties of tampons with calendered nonwoven covering web.

The invention relates generally to a tampon for feminine hygiene or medical purposes comprising a nonwoven cover having at least one, outwardly directed, smooth surface and substantially enclosing a liquid absorbing core wherein the nonwoven cover comprises at least partly thermoplastic, heat-sealable fibers the outwardly directed surface of the nonwoven cover has a coefficient of static friction of less of 0.4.

The present invention also relates generally to a process for producing a tampon for feminine hygiene or medical purposes which comprises the following steps:

a) continuously feeding an endless, liquid-absorbing sliver made of a mixture of natural and/or artificial fibers, the width of the sliver corresponding approximately to the length of the finished tampon;

b) subdividing the sliver into strips of equal lengths, which are suitable for producing tampons;

c) continuously feeding an endless, nonwoven covering web, which is at least partly composed of thermoplastic fibers and has an essentially open, liquid-permeable structure;

d) cutting the nonwoven covering web into nonwoven covering web sections;

e) shaping each of the sliver into an approximately cylindrical tampon blank with/without the nonwoven covering web section which at least partly forms an outer side;

f) compressing the tampon blank, together with the nonwoven covering web section at least partly surrounding its surface, radially in relation to its main axis, into the final shape of the tampon.

This process according to the invention is characterized in that the continuously fed, nonwoven covering web, before it is cut into individual covering web sections, is subjected to a treatment involving heat and pressure, in such a way that at least the outer surface of the nonwoven covering web, which surrounds at least a significant part of the surface of the tampon, is smoothed whilst retaining the characteristics of the nonwoven covering web and the absorption capacity of the tampon.

The following items of information, supporting the invention, were all ascertained using calendered coverings which are composed of bicomponent fibers of the PE/PET covering/core type, for which the precursor materials were air-laid nonwoven covering materials. Additionally, the fibers of the nonwoven covering to be used may be randomly oriented.

The electron-microscope images in FIG. 1 of a material based on bicomponent fibers show that the outer layers of lower melting polymer of the bicomponent fibers are plasticized by the process, so that adjacent fibers are notched at each of their crossing points, and thus the open regions of the material are retained to the greatest extent after the fibers are solidified by cooling down. The smoothing of loose fibers, compression to a common thickness and the filling of open regions all contribute to the fact that the characteristics of the surface differs considerably from the original material. The fastening of the nonwoven covering web to the tampon is still possible because of the component of low melting point which is present and, after the final product has been produced, an extremely smooth, supple surface results.

It is preferred that the physical properties of the calendered material are optimized, in order to produce the best possible balance for the efficiency of the tampon. If the basis weight is too low, there are large open regions between the calendered regions, which reduce the continuity of the surface and therefore reduce the smooth, soft feel of the tampon. If, on the other hand, the basis weight is too high, the open region is closed by calendering, the permeability of the covering is reduced and, as a result, the absorption capacity of the tampon is restricted. For the PE/PET system, a calendering temperature between 70–120° C. and a pressure of 0.2 to 2.5 bar at a passage speed of 8–12 m/min are necessary in order to achieve smoothing. Preferred operating conditions are given by 80–85° C., a pressure of 0.5 bar and a passage speed of 10 m/min. The melting point of PE in this system is 130° C.

FIG. 2 shows that the basis weight range for the primary materials is 14–17 $g/m^2$, and the thickness of the primary materials is about 0.4 mm or greater for four stacked layers of the material. The passage of the primary materials through the gap of a smoothing calender produces a material of consistent thickness of less than about 0.3 mm for four stacked layers of the material, irrespective of its initial basis weight. Preferably, the thickness of four stacked layers of the material is less than about 0.2 mm. Consequently, the density increases and the open region reduces at the same time in proportion to an increasing basis weight of the primary material.

Figure 3:
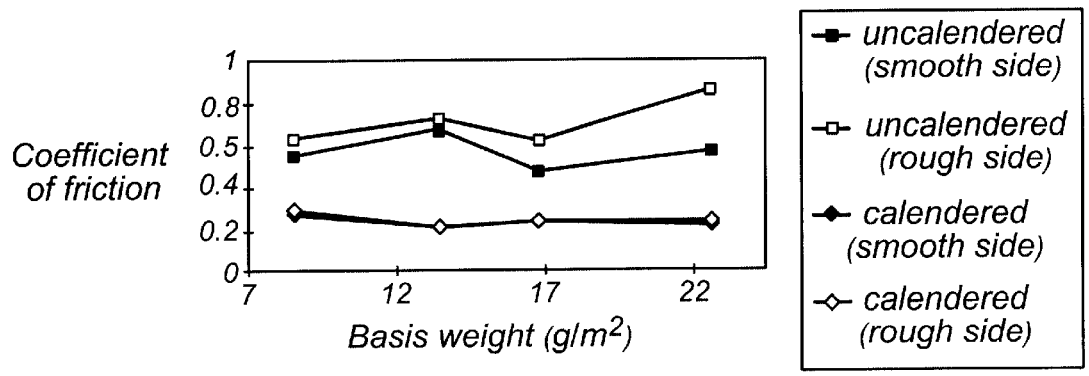

The smoothness of these materials was measured by reference to the coefficients of friction (FIG. 3). The rough and smooth sides of the original, air-laid web are calendered in the same way, in order to bring about noticeably lower frictional properties. A coefficient of friction of 0.2 corresponds to the known value for pure PE, and this value probably constitutes the maximum theoretical smoothness of this material based on PE/PET, without changing the final quality and/or quantity of fibers. It can be seen from FIG. 3 that a basis weight of 8.5 $g/m^2$ results in a rougher surface, because of the very open property of the web. It is also obvious that the use of a basis weight of more than 13.5 $g/m^2$ provides hardly any advantages, since this value provides the theoretical, maximum smoothness for this system.

Figure 4:
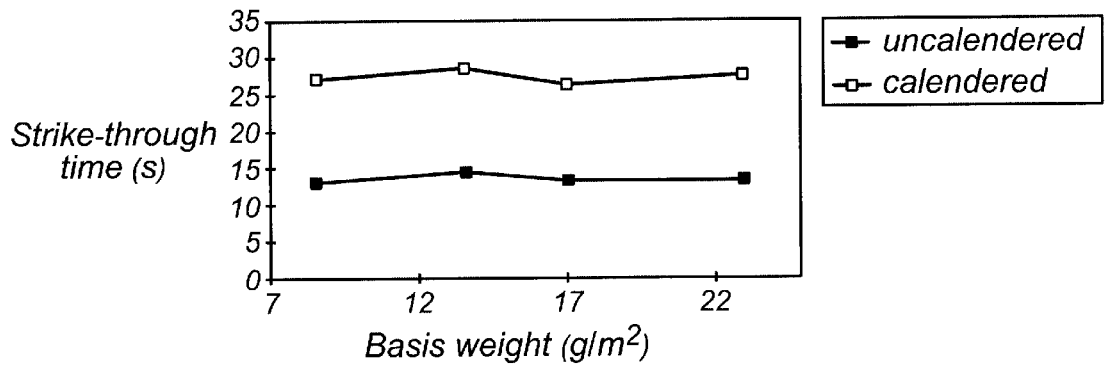

FIG. 4 shows a comparison between the strike-through times for the primary webs and calendered webs, using an artificial, high-viscosity, substitute menstrual fluid. The calendering appears to substantially increase the liquid uptake time, but according to FIG. 5, the capillary suction force appears to increase significantly. The capillary suction force can be measured in accordance to the procedure described in U.S. Pat. No. 5,817,077, which is herein incorporated by reference. These data, in conjunction suggest that while the calendering forces reduce the size of the open area of the cover material, the effective pore size of the material also decreases. This appears to offset possible losses in the liquid-through times and in use there appears to be no significance in tampon leackage and other related performance criteria.

Figure 5:
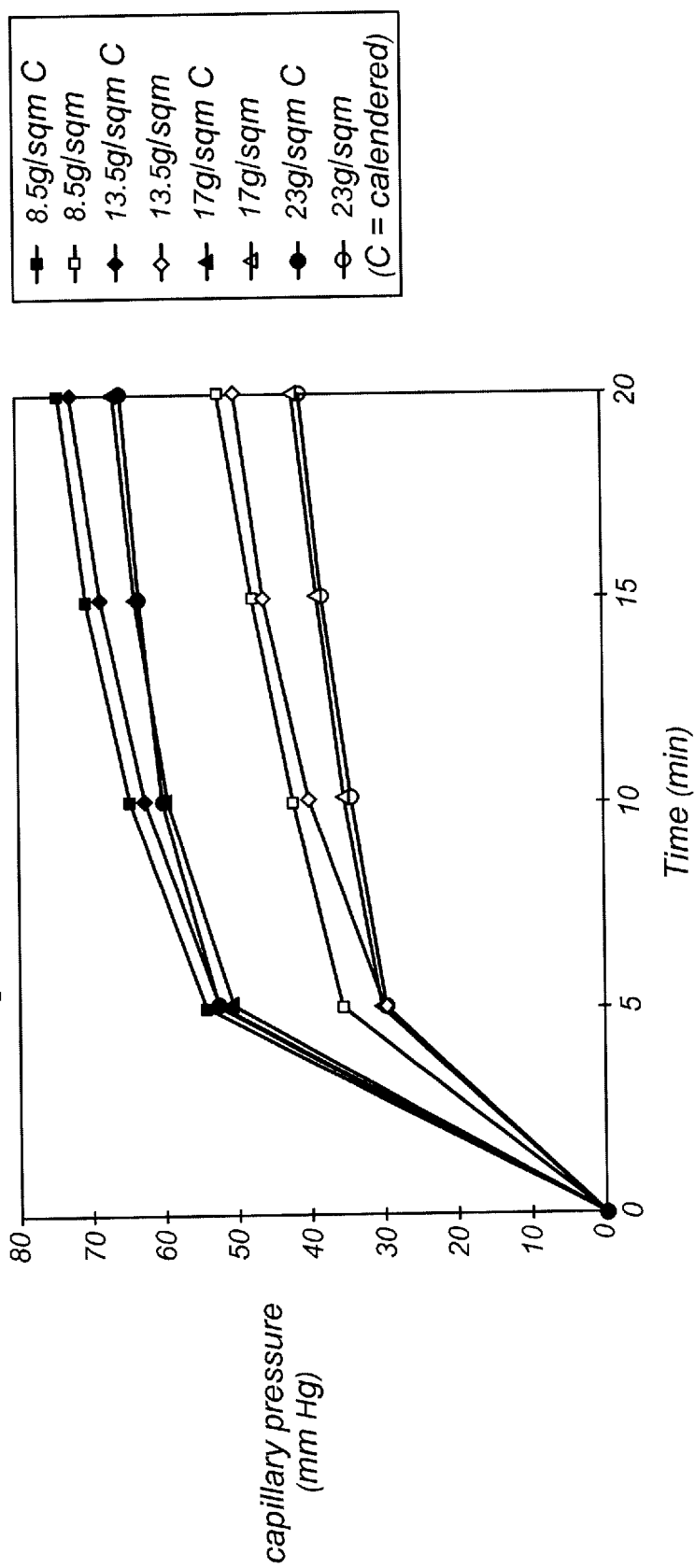
FIG. 5 shows a graphical illustration of comparative values of capillary pressures for tampons with calendered and non-calendered nonwoven covering webs.

The data on capillary forces plotted in FIG. 5 lead one to suppose that calendering reinforces the capillary suction force. Of course, the calendered covering layers exhibit higher suction forces than the original nonwoven materials or nonwovens (black symbols in comparison to white symbols). Therefore, the calendering process not only reduces the size of the open region, but also reduces the effective pore size in the nonwoven. In trials which were carried out with artificial menstrual fluid, an increase was observed in the capillary pressure which was exerted by the calendered material in comparison with uncalendered, analogous materials. This effect offsets the loss on open regions in the material, and it cannot be seen that the absorption behaviour of the tampon is influenced negatively.

Absorption Capacity

The values for absorption capacity of the tampon according to the invention that are listed below were ascertained in a test unit, which is described in European Patent No. 0 422 660 B1 (U.S. Ser. No. 07/596,454 which is herein incorporated by reference).

|  | o.b. standard | Tampon with smoothed covering |
|---|---|---|
| Weight (g) of the tampon, including retrieval string | 2.7 | 2.7 |
| Absorption capacity (ml) | 11.2 (0.3) | 11.3 (0.3) |
| Specific absorption capacity (ml/g) | 4.3 | 4.3 |
| Absorption rate (ml/s) | 2.4 | 2.1 |
| Absorption capacity for liquid of higher viscosity | 9.4 (0.4) | 9.9 (0.3) |

Coefficient of Friction

The coefficient of static friction between two identical nonwoven covering materials was determined with a static friction testing instrument generally according to the procedure described in ASTM D4918-95. A polished metal block, which is covered with the nonwoven covering material, is placed on an inclined surface, on which the nonwoven covering material is stretched out. The coefficient of friction is ascertained from the tangent of the angle of inclination at which the metal block begins to move. Preferably, the material has a coefficient of static friction of less than about 0.4, more preferably, less than about 0.3, and most preferably, less than about 0.26.

|  | Uncalendered non-woven covering material | Calendered nonwoven covering material |
|---|---|---|
| Weight (g/m$^2$) | 14 | 14 |
| Coefficient of friction | 0.6–0.7 | 0.24–0.26 |

As already indicated above, the LD poly-ethylene/polyester bicomponent fiber material which is preferably used has a weight of 11–17 g/m$^2$, preferably of 14 g/m$^2$. The tearing strength of the nonwoven covering material in the longitudinal direction is $\leq 19$ N/39 mm or $\leq 20$ N/45 mm. Elongation at break in the longitudinal direction is $\leq 55\%$. The sealing temperature of the nonwoven material is 120–140° C.

Figure 8:
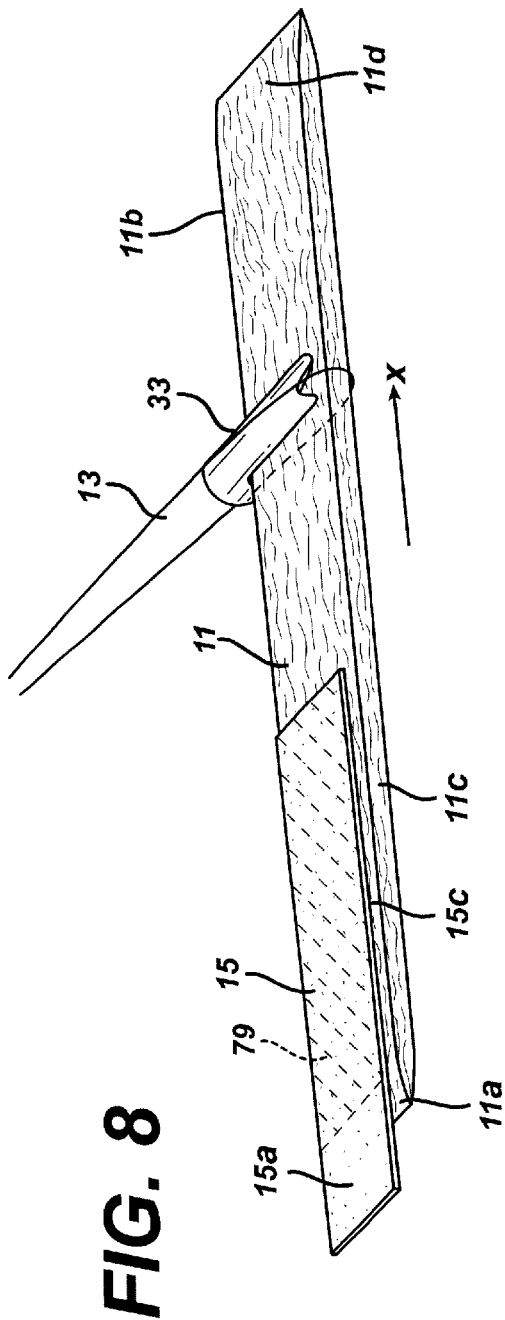
Figure 10:
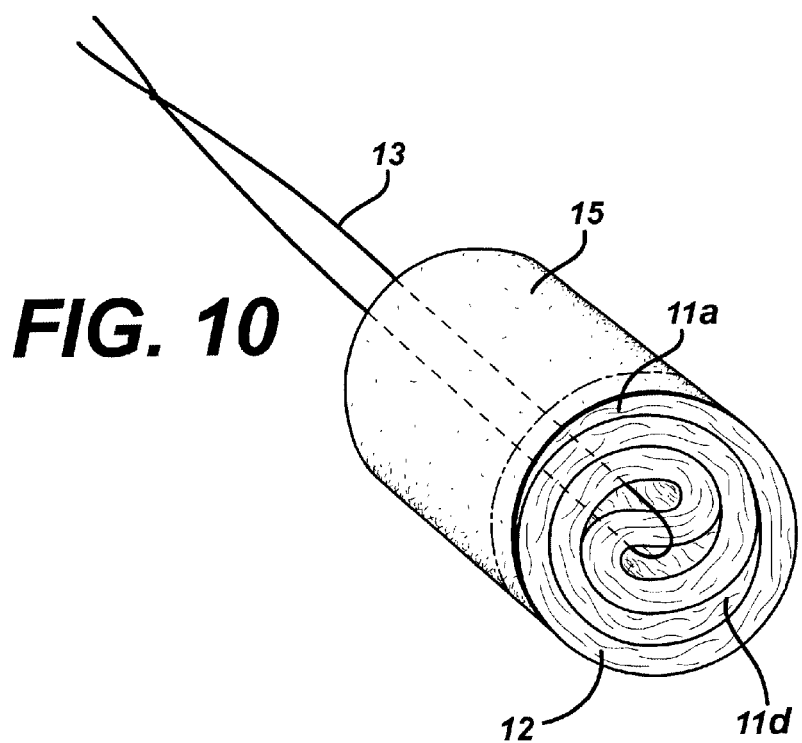
Figure 11:
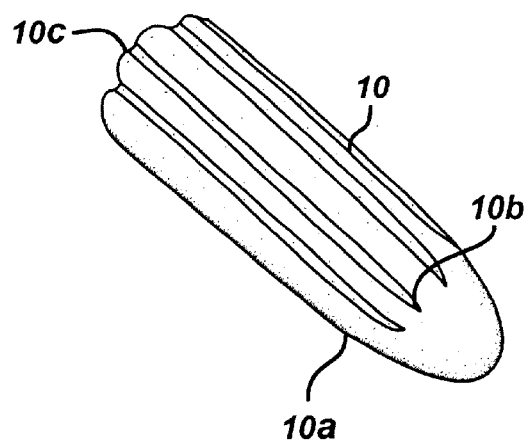

A preferred embodiment of the tampon according to the invention and specified above will be described below with reference to FIGS. 6 to 14: depicted in FIG. 11 is a tampon 10 for feminine hygiene, which consists of a section 11 of specific length, which can be seen from FIG. 8, of a calendered sliver, which is composed of a mixture of natural and thermoplastic bicomponent fibers (FIGS. 6–9). The fiber mixture preferably comprises 75% rayon fibers with an irregular, preferably multi-armed or star-shaped, for example three-armed, cross section, having an appropriately higher flexural strength, and 25% standard rayon fibers. The sliver 30 has a width which corresponds approximately to the length of the tampon 10. This sliver section 11 is essentially rolled up on itself about an axis that is located transverse to its longitudinal direction and outside the longitudinal centre of the sliver section 11, to form a tampon blank 12, and at the same time is provided with a retrieval string 13. The tampon blank 12 is pressed, essentially radially in relation to the winding axis, into the final shape of the tampon 10. By means of the pressing, the tampon 10 is provided with eight press notches, which are distributed over identical circumferential angles. An insertion end 10a of the tampon 10 is designed as a taper 10b tapering sharply to a point, whose form is comparable with that of the tip of a bullet. Other tampon forms, including those such as are described in U.S. Pat. No. 4,863,450 may also be used with this invention.

According to FIG. 7, a nonwoven covering web section 15 made of liquid-permeable, thermoplastic material is sealed onto that part of the sliver section 11 which forms the circumferential surface of the tampon 10, using heat and pressure, this nonwoven covering web section 15 being longer than the circumference of the tampon blank 12, however. According to the invention, this nonwoven covering web section 15 is provided on both sides with an extremely smooth surface as a result of the additional calendering operation mentioned further above. The smoothness of the outer surface of the nonwoven covering web section 15 serves the purpose of making the insertion of the tampon into the bodily cavity significantly easier, even outside the time of heavier menstruation.

Figure 9:
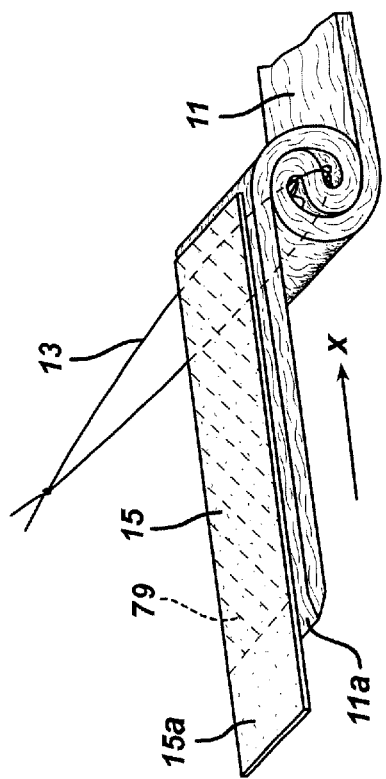

FIGS. 7 to 9 show that the thermoplastic nonwoven covering web section 15 is firmly connected to the sliver 30 preferably by means of parallel weld lines 79 at a distance from one another, these weld lines forming an acute angle with the longitudinal direction of the sliver 30. The distances between the individual weld lines 79 are such that, between the weld lines 79, the liquid-permeable material of the nonwoven covering web section 15 rests closely on the sliver material. Other attachment patterns may also be used, such as discontinued dots, etc. This ensures that liquid which arrives on the nonwoven covering web section 15 on the circumferential surface of the tampon is immediately drawn into the interior of the tampon as a result of the capillary action of the fiber material in the woven tape section 11 located underneath. If appropriate, it is possible for the nonwoven covering web section 15 also to be applied to the sliver 30 by needling or fastened thereto, for example by mechanical or adhesive means.

The outer end 15a of the nonwoven covering web section 15 extends beyond the outer end 11a of the sliver section 11, and is welded, using heat and pressure, to the outside of a portion of the nonwoven covering web section 15 that is sealed onto the sliver section 11.

It can be seen that the thermoplastic, liquid-permeable nonwoven covering web section 15 is preferably narrower than the width of the sliver section 11, but is flush with that longitudinal edge 11b of the sliver section 11 which forms the retrieval end 10c of the tampon 10. The longitudinal edge 11c of the sliver section 11 that forms the insertion end 10a of the tampon 10 projects over the associated edge 15c of the liquid-permeable, thermoplastic nonwoven covering web section 15 to a width which approximately corresponds to the height of the taper 10b, running to a point, on the tampon 10 at the insertion end 10a. The liquid-permeable nonwoven covering web 32 (FIG. 12) is at least predominantly composed of thermoplastic, nonwoven fiber material, which is preferably produced from a bicomponent fiber whose components consist, for example, of a polyester core and an HD polyethylene sheath. Other materials such as other forms of polyethylene, polypropylene, ethylene-vinyl acetate copolymers and other, relatively low melting point materials may also be used. It is particularly expedient if the high-pressure polyethylene has a lower melting point than the polyester. Since the free, outer end 15a of the thermoplastic nonwoven covering web section 15 is welded to the outside of that longitudinal section of the nonwoven covering web section 15 which is sealed onto the sliver section 11, in the circumferential direction of the tampon blank 12, the nonwoven covering web section 15 forms a covering which is firmly connected to the latter and whose outer diameter corresponds to that of the tampon blank.

A preferred process for producing the above-described tampon comprises the following steps, which are described below with reference to FIGS. 6 to 14:

According to FIG. 6, a calendered sliver 30, which consists of a mixture of natural or cellulose fibers which preferably have an irregular cross section, for example one having a plurality of arms, and which has a width corresponding to the length of the tampon 10, is fed continuously. The sliver 30 is weakened transversely to its longitudinal direction, in each case by so-called weakening points 31, for example by being perforated, between sections 11 of a length which is needed for the production of the tampon 10. This weakening is additionally achieved by stretching the sliver 30, so that a thinning of the sliver 30 or a reduction in its cross section, but no severing of the sliver 30, occurs in the stretched zone or at the weak point 31. The sliver 30 is moved on continuously in the direction of the arrow x.

Approximately at the same time, a continuously fed nonwoven covering web 32 (FIG. 12) made of thermoplastic, liquid-permeable, nonwoven covering web, which according to the invention has been subjected to calendering involving the application of pressure and heat, is in each case cut into a nonwoven covering web section 15, whose length exceeds the circumference of the tampon blank 12 shown in FIG. 10. The liquid-permeable, thermoplastic nonwoven covering web section 15 is then fastened, for example by sealing or needling, onto the outside of a region of the sliver 30 which is located at the rear in the direction of movement x of the sliver 30 and in front of a weak point 31, with the exertion of heat and pressure, along parallel weld lines 79 which run obliquely in relation to the longitudinal direction of the sliver 30. The arrangement of the nonwoven covering web section 15 on the upper side of the sliver 30 is in this case provided such that the end 15a of the nonwoven covering web section 15 which is on the outside and at the rear in the direction of movement x of the sliver 30 (FIG. 8) extends freely, that is to say without being sealed, beyond the weak point 31 in the sliver 30. The sliver 30 is then cut through at the weak point 31, so that the sliver section 11 is produced.

The sliver section 11 is then essentially rolled up on itself, according to FIG. 9, to form a tampon blank 12, which is shown in FIG. 10, about an axis which runs transversely in relation to its longitudinal direction and is represented in FIG. 8 by a winding mandrel 33. Rolling up the sliver section 11 is carried out such that, in the circumferential direction of the tampon blank 12, one end 11a of the outer layer of the rolled-up sliver section 11 overlaps the other end lid (see FIGS. 8 and 10) of the layer of the rolled-up sliver section 11 that is located underneath. By this means, a more uniform material distribution on the outer circumference of the tampon blank 12 and, consequently, an essentially cylindrical shape of the same, are achieved.

As can be seen from FIG. 10, the length of the thermoplastic, liquid-permeable nonwoven covering web section 15 is such that the latter completely encloses the circumference of the tampon blank 12 to the envisaged width, the free or unsealed end 15a initially still projecting at the outside. The winding operation is now completed by this free, unsealed end 15a of the nonwoven covering web section 15 being welded, with the exertion of heat and pressure, onto that portion, adjacent in the circumferential direction of the tampon blank 12 to the outer end of the sliver section 11, of the thermo-plastic nonwoven covering web section 15 which is sealed onto the sliver section 11. Since, in the process, the surfaces of HD polyethylene of the melt fibers come to rest on one another, the sealing pressure does not need to be so high, in order to achieve good sealing, as in the case of the previous sealing of the nonwoven covering web section 15 onto the sliver 30.

According to FIG. 8, before the winding operation, a retrieval string 13 is laid around the sliver section 11, transversely to the longitudinal direction of the latter, and, if necessary, subsequently knotted at its free end. The tampon blank 12, finished by being wound up into a cylindrical shape, is then fed to a press, which preferably comprises eight press jaws arranged in a star shape, by means of which the tampon blank 12 is pressed essentially radially into the final shape of the tampon 10 illustrated in FIG. 11.

After that, the insertion end 10a of the tampon is shaped into a taper 10b, running to a point and resembling a bullet or a dome, in order to make the insertion of the tampon into the bodily cavity still more agreeable. For the present process, it is not significant where and how the retrieval string 13 is applied in detail and whether the insertion end is domed or not.

It goes without saying that the length of the nonwoven covering web section 15 depends on the final diameter of the tampon blank 12. Also dependent on this is the length of the freely projecting, unsealed end 15a of the nonwoven covering web section 15, which is generally between 20 and 50 mm.

It can be seen from FIGS. 7 to 11 that the outside of the sliver 30 is covered by the liquid-permeable, thermoplastic nonwoven covering web section 15 to a width which extends, from that longitudinal edge 30b of the sliver 30 which forms the retrieval end 10c of the tampon 10, only as far as into the vicinity of that longitudinal edge 11c of the sliver section 11 which forms the insertion end 10a of the tampon 10. The longitudinal edge 11c of the sliver 30 which is not covered by the thermoplastic nonwoven covering web section 15 is sufficiently wide that it can be shaped in order to form the taper or dome 10b, running to a point, of the insertion end 10a of the tampon 10 following the pressing of the tampon blank 12 into the final shape of the tampon 10. At the same time, it is ensured that the insertion end 10a of the tampon 10, which is free of the nonwoven covering web section 15, is acted on directly by the bodily fluid to be taken up, and consequently the tampon is able to expand without delay and, as a result, is able to develop its full absorbency and can undertake the complete protective function for the user.

Figure 12:
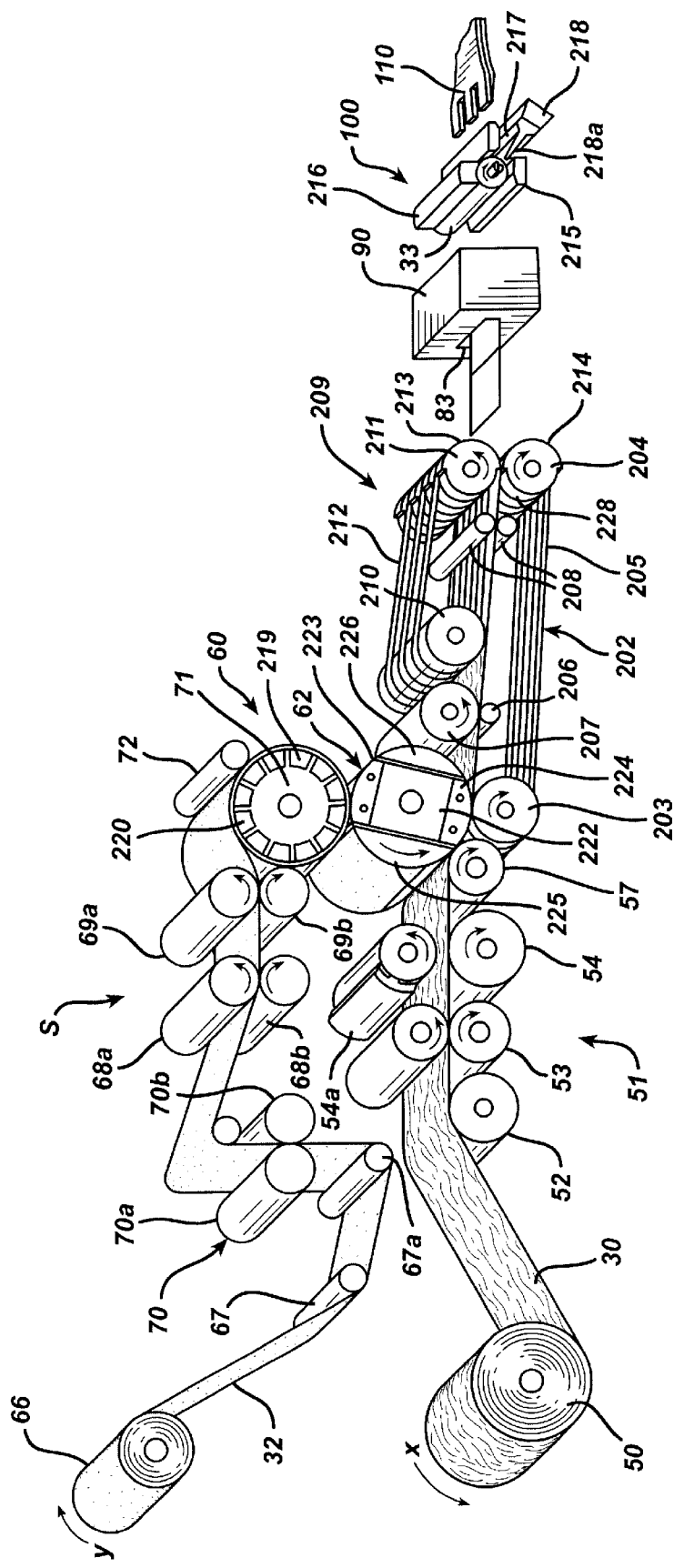
FIG. 12 shows a first embodiment of an apparatus for producing a first tampon according to the invention in a diagrammatic view, with which apparatus tampons with a covering can be produced.

FIG. 12 shows an apparatus for producing the tampon by using the specified process according to the invention. Illustrated in the left-hand part of the drawing is a calendered sliver 30 made of the above-described fiber mixture, which is fed continuously from a supply reel 50, in the direction of movement x, to a weakening station 51. The weakening station 51, which is preceded by a supporting roller 52, comprises, in the direction of movement x of the sliver 30, a pair of perforating and clamping rollers 53 and a pair of stretching rollers 54. Since the perforating and clamping rollers 53 hold the sliver 30 firmly upstream of the stretching rollers 54 at the instant of stretching, and the stretching rollers 54, with their stretching jaws 54a, bring about an acceleration of the sliver 30 gripped by them in the transport direction x, the sliver 30 is thinned or reduced in cross section on the path between the perforating and clamping rollers 53 and the stretching rollers 54, so that the weak point 31 is produced. Connected downstream of the stretching roller pair 54, 54a, on the underside of the sliver 30, is a smooth, cylindrical pressure roller 57, which co-operates with an essentially cylindrical sealing or calendering roller 62 on the upper side of the movement path of the sliver 30, and forms with the said roller 62 a sealing or calendering station 60. The roller 62 can be heated in a suitable way, for example by means of electrical resistance heating, and can be driven in an anticlockwise direction.

It can be seen that, upstream of the sealing station 60 and above the sliver 30 and the weakening station 51, there is provided a supply reel 66 for a continuous strip 32 of nonwoven, liquid-permeable and thermoplastic bicomponent fibers, whose basis weight is, for example, 14 g/m². The nonwoven strip 32 is fed, via spring-mounted turn rollers 67, 67a, to a calender stack 70 provided according to the invention. The calender stack 70 comprises two smooth, cylindrical, heatable pressure rollers 70a, 70b, which act on the nonwoven covering web 32 at a temperature of 70–100° C., preferably 80–85° C., and a pressure of 0.5–2.5 bar, in order to provide said web, both on the upper side and on the underside, with a soft, smooth surface structure, which corresponds to a significantly reduced coefficient of friction of preferably 0.2, as equivalent to the known value of pure polytetrafluoroethylene on steel, and exhibits the maximum theoretical smoothness and softness.

A cutting station S comprises a pair of transport rolls 68a, 68b, which are arranged above and beneath the nonwoven covering web 32 and are driven in opposite directions, and a pair of cutting rolls 69a, 69b, which are arranged after the former, which are likewise driven in opposite directions and of which the knife roll 69 is provided over a significant portion of a generatrix with cutters for cutting through the predominant part of the strip 32. The circumferential speed of the transport rolls 68a, 68b and cutting rolls 69a, 69b corresponds approximately to half the transport speed of the sliver 30, such that the nonwoven covering web 32 can be drawn off continuously from the supply reel 66, in the direction of the arrow y, at a speed which corresponds to the length of the nonwoven covering web section 15 of the nonwoven material to be applied.

The cutting rolls 69a, 69b cut essentially, but not completely, through the nonwoven covering web 32 in the transverse direction, so that the nonwoven covering web section 15, which was formed by the cutting and is running forward, is still connected to the following nonwoven covering web via a few so-called webs.

Connected downstream of the cutting station S is a vacuum roller 71. Arranged in the interior of the vacuum roller 71 is a slide 219, which remains stationary and is provided over about 180° of its circumference with lateral suction openings (not shown), which make a suction action possible via smaller suction openings 220, adjacent to the former openings, in the circumferential wall of the vacuum roller 71.

The vacuum roller 71 is assigned an acceleration roll 72 of smaller diameter on the upper side, which serves to press the nonwoven covering web against the vacuum roller 71. The circumferential speed of the vacuum roller 71 and of the acceleration roll 72 corresponds to the transport speed of the sliver 30. Therefore, the nonwoven covering web section 15 coming from the cutting station S can be drawn by suction against the circumference of the vacuum roller 71 and, in a stretched position, can be carried along in the clockwise direction into the gap which the vacuum roller 71 forms with the acceleration roll 72. As soon as the leading end of the nonwoven covering web section 15 gets into the gap between the acceleration roll 72 and the vacuum roller 71, the nonwoven covering web section 15 is accelerated to twice the speed, namely the sliver speed, and is consequently completely torn off the following nonwoven covering web 32 in the region of the cut point which was produced in the cutting station S.

The vacuum roller 71 now carries with it the nonwoven covering web section 15 that is attached to its circumference by suction to the gap which the vacuum roller 71 forms with the sealing roller 62. Since the vacuum roller 71 touches the sealing roller 62 on its upper side, and at this point the vacuum is blocked off in the direction of rotation of the vacuum roller 71, as described further below, the thermoplastic nonwoven covering web section 15 is carried along by adhesion, and heated, at the earliest possible point in time by the heated sealing roller 62. Consequently, the nonwoven covering web section 15, as it continues to be carried along through the gap between sealing roller 62 and vacuum roller 71, when it encounters the surface of the sliver 30, has been preheated to such an extent that the lower melting point covering layer of the melt fibers of the nonwoven covering web section 15 melt in the region of the nip between the pressure roller 57 and the sealing roller 62 and, as a result of the correct setting of pressure and temperature, an intimate connection to the fibers on the surface of the sliver 30 is produced.

A pressure roller 57 is connected immediately downstream of the weakening station 51.

Accordingly, only the sealing roller 62 is provided for the sealing. The sealing roller 62 has a particular structure that makes it possible to perform the sealing only over a part of the circumference of the sealing roller 62, by means of heatable sealing elements 223, 224, which are arranged diametrically opposite each other on a basic body 222 and are profiled to correspond to the welding or sealing pattern. The circumferential length of the sealing elements 223 and 224 in each case corresponds precisely to the length of a nonwoven covering web section 15 which is to be sealed onto the sliver section 11. Two non-heated insulating elements 225, 226 are fastened to the basic body 222, being offset by 90° with respect to the diametrically opposite sealing elements 223, 224. The circumferential curves of the insulating elements 225, 226 have the same radius as the outer surfaces of the sealing elements 223, 224, so that the result is a circumferential surface made up of circular sectors of identical radius. The arrangement of the insulating elements 225, 226 ensures that, in each case, the free or unsealed end 15a of the thermoplastic nonwoven covering web sections 15 which project over the sealing elements 223 and 224 in the direction opposite the direction of rotation of the sealing roller 62 comes to lie on one of the insulating elements 225, 226 and, consequently, is not sealed to the sliver 30.

At the level of the sealing roller 62, underneath the movement path of the sliver 30, there is a belt conveyor 202, which comprises a large number of front drive pulleys 203 and rear turn pulleys 204, which each carry endless guide belts 205.

The guide belts 205 are supported in the upper belt run by a supporting roller 206, which is located opposite a pressure roller 207 of significantly greater diameter on the upper side of the movement path of the sliver 30. The supporting roller 206 and the pressure roller 207 are clamped against each other, so that the sliver 30 is firmly held when the sliver section 11 located behind it in the direction of movement is being drawn out of the transport system by means of a transport and separating tongs mechanism 110 which is provided downstream of the belt conveyor 202.

Assigned to the upper run of the guide belts 205 is a pair of tensioning rollers 208, from which the upper run of the guide belts 205 is deflected obliquely downwards in the direction towards the turn pulleys 204.

Above the movement path of the sliver 30 there is a guide device 209, which likewise comprises a number of turn pulleys 210, 211, which are offset axially at a distance from one another and on which in turn, axially offset, endless belts 212 are arranged, each being arranged above the guide belts 205 of the lower belt conveyor 202. The front turn pulleys 210 of the rear guide device 209 are located close behind the pressure roller 207, while the rear turn pulleys 211 are arranged above the rear turn pulleys 204 of the belt conveyor 202. In the direction of movement of the sliver 30, the upper run of the guide belts 205 and the lower run of the endless belts 212 form a free gap 228, into which the gripping tongs 110 can be moved through the opening 83 in a retrieval-string fitting and knotting device 90, as will be explained below.

The rear turn pulleys 211 and 204 of the upper guide device 209 and the lower belt conveyor 202 are provided, in each case at 180°, with radially outwardly projecting guide segments 213 and 214. The guide segments 213 and 214 run in synchronism with one another and carry or guide the sliver 30. When the transport and separating tongs mechanism 110 moves, counter to the transport direction x of the sliver 30, in the direction of the gap 228 between the turn pulleys 211 and 204, said mechanism grips the leading end of the sliver 30 and pulls this, at a speed which is increased with respect to the transport speed of the sliver, into the active range of the retrieval-string fitting and knotting device 90 and of a winding station 100. Since the pressure roller 207 with the supporting roller 206 is located at a distance from the gap 228 for gripping the leading end of the sliver 30 by means of the transport and separating tongs mechanism 110, which distance is greater than the length of a sliver section 11, the weak point 31 on the sliver 30 is in each case located behind the pressure roller 207 and the supporting roller 206, with the result that the transport and separating tongs mechanism 110 pulls away that section of the sliver 30 that extends behind the pressure roller 207, as far as the weak point 31, and tears it at the weak point 31. After the sliver section 11 has been separated in this way, it is guided by means of the transport tongs mechanism 110 into the region of the retrieval-string fitting and knotting device 90 and of the winding station 100. While the fitting of the retrieval string 13 and the knotting of the same can take place as described below, the winding station 100 is equipped with a winding mandrel 33 (FIGS. 3 and 12), which can be moved axially to and fro and can be driven in rotation. Provided in the winding station 100 are wiping pads 215, 216 for sealing the free, projecting end 15a of the nonwoven covering web section 15 to that portion of the nonwoven covering web section 15 which is fastened to the tampon blank 12.

The lower and upper wiping pads 215, 216 are arranged at a radial distance from the winding mandrel 33, it being preferably possible for only the lower wiping pad 215 to be heated, this extending over an angle of about 190 to 280° in the 3rd quadrant of a circle. A heatable sealing element 218 is arranged so that it can move to and fro with respect to the winding mandrel 33 through an aperture 217 in the lower wiping pad 215, the said sealing element being provided in order to seal the previously unsealed, rear end 15a of the nonwoven covering web section 15 to a portion of the nonwoven covering web section 15 that is fastened to the circumference of the tampon blank 12. Since the end face 218a of the sealing element 218 is narrow, it is made possible to weld the outer edge of the free end 15a of the nonwoven covering web section 15 only along a generatrix to the material of the same nonwoven covering web section 15 that is fastened to the circumference of the tampon blank 12.

The cutting rolls 69 cut through the nonwoven covering web 32 significantly but not completely, so that, on each side of this cut, the nonwoven covering web 32 remains connected via material webs (not shown), in a manner similar to that in the case of a perforation. The acceleration roll 72 arranged downstream is driven with a rotational speed which corresponds to the circumferential speed of the vacuum roller 71 and hence to the transport speed of the sliver 30. If the leading end of the nonwoven covering web 15 comes into the active range of the acceleration roll 72, that section of the nonwoven covering web 32 which is located upstream of the cut point is torn off and accelerated to the sliver speed in such a way that the individual nonwoven covering web sections 15 are led, at the respectively correct distance from one another, up to the leading end, in the direction of rotation, of one of the two sealing elements 223, 224.

The nonwoven covering web 32 located downstream of the tearing point is always smoothed and stretched in the transport direction as a result of the suction action of the vacuum roller 71. Because of the extremely low mass of the separated nonwoven covering web section 15, the latter is accelerated abruptly to the sliver speed, so that an always accurate positioning of the nonwoven covering web section 15 on the vacuum roller 71 can be achieved.

FIG. 13 shows an alternative embodiment of an assembled tampon 300 before its diameter is reduced to the standard size. It comprises an essentially cylindrically shaped tampon blank 311 made of gauze, muslin, wadding or a similar absorbent material. The tampon blank 311 is enclosed by a cup-like covering 312, which has an annular rim 312a (FIGS. 14 and 15) and extends beyond the corresponding end surface 311c of the tampon blank 311. As can be seen from FIGS. 13 and 15, the opposite end surface 311b of the tampon blank 311 adjoins the bottom end wall 312b, which resembles a circular area, of the nonwoven covering web 312; the outer surface 311a of the cylindrical tampon blank 311 is completely surrounded by a tubular wall 312c, consisting of a number of sections, of the nonwoven covering web 312.

In addition, the tampon 310 has a retrieval string 313, which has an end 313a which is shaped like a loop, which is fastened to the tampon blank 311 in the region of the end surface 11c, and extends through the tubular wall 312c of the nonwoven covering web 312 and away from the latter. The retrieval string 313 is provided with a knot 313b, whose formation is disclosed, for example, by U.S. Pat. No. 4,312,587, which is herein incorporated by reference.

The tubular wall 312c of the nonwoven covering web section 312 comprises two essentially semicylindrical shells or trough-like main sections 312d having edge regions 312f which overlap and which extend axially parallel to the axis of the cylindrical tampon blank 311 and of the nonwoven covering web section 312, from the bottom end wall 312b, in the direction of the end surface 311c of the tampon blank 311, and beyond the end surface 311c, in order to form the annular rim 312a. The tubular wall 312c of the nonwoven covering web 312 also comprises two additional, essentially concave/convex (hollowly raised) sections 312e, one of which is illustrated in FIG. 14, and which alternate with the sections 312d and extend from the bottom end wall 312b in the direction of the end surface 311c.

When the forming of a polygonal, preferably rectangular, nonwoven covering web section 412 (FIG. 16) from liquid-permeable nonwoven covering web material has been finished, an annular rim 412a is folded over the end surface 311c of the tampon blank 311, in the direction which is indicated by the arrow 312g in FIG. 16, so that the cup encloses the end surface 311b, the entire circumferential surface 311a and at least part, preferably at least the major part, of the end surface 311c of the tampon blank 311, so that the fibers of the latter do not come into contact with the skin or with the tissue of the bodily cavity into which the finished tampon is inserted, either by hand or by a standard applicator. Use is preferably made of a rectangular nonwoven covering web section 412, in which the length of the two long sides 412c is at least 1.5 times as great as the length of one of the narrow sides 412d. The sides 412c and 412d surround part 312b of the nonwoven covering web section 412, which for its part surrounds a central part 312a which is shaped like a circular area.

FIG. 16 also shows a tubular folding die plate 314, which is used to form the wrapper 312 in the nonwoven covering web section 312. The die plate 314 is composed of four parts 314a, 314b, 314c, 314d, which form a tubular guide for the tampon blank 311. The inlet to the tubular guide of the die plate 314 is designed as a truncated cone, in order to make the insertion of the tampon blank 311 into the die plate 314 easier. The tampon blank 311 does not come into contact with the parts 314a, 314b, 314c, 314d of the die plate 314, since a central portion 312h of the wrapper 312 is inserted by way of its end face 311b into the die plate, so that the central portion 312h is pushed through the die plate 314, the second or remaining portion 312i of the nonwoven covering web section 312 being automatically placed around the outer surface 311a of the tampon blank 311, in order to form the tubular wall 312c having the rim 312a. The manner in which the rim 312a is then folded into the cup shape, over the end surface 311c of the tampon blank 311, by means of suitable folding arms or in any other way, is not shown in detail. Folding of this type takes place in the directions of the arrows 312g, and is normally associated with a simultaneous reduction in the diameter of the cup shape. After the retrieval string 313 has been fastened, the tampon blank 311 surrounded by the cup-like nonwoven covering web section 312 is then compressed, radially in relation to the main axis of the tampon blank 311, into the final shape of the finished tampon, whilst reducing the diameter of the tampon blank 311. The nonwoven covering web section 312 is preferably cut off the leading end of a liquid-permeable nonwoven covering web that is continually fed from a supply reel. As FIG. 16 shows, the nonwoven covering material is advantageously held in a vertical plane when its central portion 312h is adjacent to the inlet of the tubular die plate 314 and the other side of the central portion 312h is adjacent to the end surface 311b of the tampon blank 311. The advancing movement of the tampon blank 311 is provided by a plunger (not illustrated), in order to push the nonwoven covering web section 312 into the die plate 314, and in so doing to mould the cup shape.

The process for converting the nonwoven covering web section 312 into the cup shape surrounding the tampon blank 311 is carried out by an automatic machine, which preferably produces a large number of tampons per unit time, and is provided with automatic devices for pressing the tampon for the purpose of reducing the diameter of the tampon blank 311, together with the nonwoven covering web section 312 surrounding it, and at the same time for the purpose of folding the edges 312a and for the subsequent fitting of the retrieval string 313. The pressing or compressing step may be carried out simultaneously with or before or after the forming of a sharply tapered insertion end in the region of the end surface 311c of the tampon blank 311, in order to make the insertion of the finished product into a bodily cavity easier. For instance, each nonwoven covering web section 312 may be about 130 mm long and 120 mm wide, that is to say the length may be a multiple of the width. Such nonwoven covering web sections 312 can be converted into a cup shape, this being shown in FIGS. 15 and 16. A nonwoven covering web section 312 which has the above-mentioned dimensions is able to enclose a tampon blank 311 considerably more advantageously than a square wrapper, whose dimensions would all have lengths of 95 mm, although the area (7800 mm$^2$) of the rectangular wrapper is much smaller than the area (9025 mm$^2$) of the square wrapper. The saving on wrapping material is thus 14%. A further significant advantage of the tampon improved in accordance with the invention and of the production process resides in the fact that the tampon can be produced in the available covering arrangement modules of tampon production machines. All that is necessary is to connect a calendering unit, for smoothing the nonwoven covering material in accordance with the invention, between a supply reel for the continuous feed of the liquid-permeable nonwoven covering web and a cutting station for producing the nonwoven covering web sections. Likewise, existing devices for producing applicators for the tampons do not need any further changes.

The specification above is presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon for feminine hygiene or medical purposes comprising a nonwoven cover having at least one, outwardly directed, smooth surface and substantially enclosing a liquid absorbing core wherein the nonwoven cover comprises a smooth calendered nonwoven web comprising a bicomponent fiber having at least two different melting points, and the outwardly directed surface of the nonwoven cover has a coefficient of static friction of less than about 0.4.

2. The tampon of claim 1 wherein the thickness of the nonwoven cover is less than about 0.125 mm.

3. The tampon of claim 2 wherein the thickness of the nonwoven cover is less than about 0.05 mm.

4. The tampon of claim 1 wherein the coefficient of static friction is less than about 0.3.

5. The tampon of claim 4 wherein the coefficient of static friction is less than about 0.26.

6. The tampon of claim 1 wherein said bicomponent fibers comprise a polyester core.

7. The tampon of claim 6 wherein said bicomponent fibers comprise a material selected from the group consisting of polyethylene, polypropylene, and ethylene-vinyl acetate copolymers.

8. The tampon of claim 1 wherein said liquid absorbing core comprises a mixture of natural and thermoplastic fibers.

9. The tampon of claim 1 wherein the nonwoven cover has a consistent thickness.

10. The tampon of claim 1 wherein the nonwoven cover is glossy.

11. The tampon of claim 1 wherein the nonwoven web is calendered by the application of heat and pressure.

12. The tampon of claim 11 wherein the nonwoven cover is attached to the liquid absorbing core by attachment means.

13. The tampon of claim 12 wherein the attachment means include sealing or needling.

14. The tampon of claim 11 wherein the calendered nonwoven web has been compressed to a substantially uniform thickness.

15. The tampon of claim 11 wherein the nonwoven web is calendered by two smooth, heatable pressure rollers.

* * * * *